(12) United States Patent
Xu et al.

(10) Patent No.: US 7,001,745 B1
(45) Date of Patent: Feb. 21, 2006

(54) INTEIN MEDIATED PEPTIDE LIGATION

(75) Inventors: Ming-Qun Xu, Hamilton, MA (US); Thomas C. Evans, Somerville, MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/786,009

(22) PCT Filed: Sep. 30, 1999

(86) PCT No.: PCT/US99/22776

§ 371 (c)(1), (2), (4) Date: Apr. 17, 2001

(87) PCT Pub. No.: WO00/18881

PCT Pub. Date: Apr. 6, 2000

Related U.S. Application Data

(60) Provisional application No. 60/102,413, filed on Sep. 30, 1998.

(51) Int. Cl.
| | |
|---|---|
| C12P 21/04 | (2006.01) |
| C12P 21/06 | (2006.01) |
| C12N 15/63 | (2006.01) |
| C12N 15/74 | (2006.01) |
| C12N 15/79 | (2006.01) |

(52) U.S. Cl. .................. 435/69.7; 435/68.1; 435/252.3; 435/320.1

(58) Field of Classification Search ................ 435/69.7, 435/68.1, 252.3, 320.1, 471; 530/350, 402, 530/412, 413; 536/23.4

See application file for complete search history.

(56) References Cited

U.S. PATENT DOCUMENTS

| | | | | |
|---|---|---|---|---|
| 5,496,714 A | | 3/1996 | Comb et al. ............... | 435/69.7 |
| 5,789,578 A | * | 8/1998 | Burton et al. .................. | 536/56 |
| 5,834,247 A | | 11/1998 | Comb et al. ............... | 435/69.7 |
| 6,184,344 B1 | * | 2/2001 | Kent et al. ................... | 530/323 |
| 6,310,180 B1 | * | 10/2001 | Tam ........................... | 530/339 |
| 6,326,468 B1 | * | 12/2001 | Canne et al. ............... | 530/333 |

OTHER PUBLICATIONS

The Dictionary of Organic Compounds, Chapman & Hall, New York, Sixth Edition, 1996, vol. Four, p. 4155.*
Smith, D.R., et al., 1997, "Complete genome sequence of Methanobacterium thermoautotrophicum delta H. Functional analysis and comparative genomics", The Journal of Microbiology, vol. 179, pp. 7135–7155, see Fig. 8 at p. 7152.*
Chong, S., et al., Sep. 1996, "Protein splicing involving the *Saccharomyces cerevisiae* VMA intein". The Journal of Biological Chemistry, vol. 271, pp. 22159–22168.*
Chong, S., et al., Jun. 1997, "Single–column purification of free recombinant proteins using a self–cleavable affinity tag derived from a protein splicing element", Gene. vol. 192, pp. 271–281.*
Mills, K. V., et al., Mar. 1998, "Protein splicing in trans by purified N– and C– terminal fragments of the *Mycobacterium tuberculosis* RecA Intein". Proceedings of the National Academy of Sciences, U.S.A.. vol. 95. pp. 3543–3548.*
Severinov, K., et al., Jun. 1998, "Expressed protein ligation, a novel method for studying protein–protein interactions in transcription", The Journal of Biological Chemistry, vol. 273, pp. 16205–16209.*
Chong, et al., Gene, 192:271–281 (1997).
Dawson, et al., Science, 266:776–779 (1994).
Evans, et al., J. of Biological Chemistry 274:18359–18363 (1999).
Evans, et al. Protein Science 7:2256–2264 (1998).
Ito, et al., Nucleic Acids Res. 20:705–709 (1988).
Kent, Ann. Rev. Biochem. 57:957–989 (1988).
Muir, et al., Proc. Natl. Acad. Sci. USA 95:6705–6710 (1998).
Noren, et al., Science 244:182–188 (1989).
Offord, Protein Engin. 1:151–157 (1987).
Perler, et al. Nucleic Acids Res. 22:1125–1127 (1994).
Roy, et al., Methods in Enzymol. 231:194–195 (1994).
Telenti, et al. J. of Bacteriology 179:6378–6382 (1997).
Wallace, FASEB, 7:505–515 (1993).
Wieland, et al., Liebigs Annalen der Chemie, 583:129–149 (1953).

* cited by examiner

*Primary Examiner*—Ponnathapura Achutamurthy
*Assistant Examiner*—William W. Moore
(74) *Attorney, Agent, or Firm*—Harriet M. Strimpel

(57) ABSTRACT

The present invention provides methods that utilize compositions containing colostrinin, an constituent peptide thereof, an active analog thereof, and combinations thereof, as an oxidative stress regulator.

16 Claims, 11 Drawing Sheets

DIRECT LIGATION REACTON

FIG. 5A

DNA Sequence of pTXB1 plasmid

```
 140- 997 beta-lactamase (Ap)
1042-1555 M13 origin
2254      ColE1 origin
2626-2814 rop
3376-4455 lacIq
5440-5456 T7 promoter
5440-5459 T7 universal primer (forward)
5457      first nucleotide of the T7 transcript
5459-5483 lac operator
5513-5519 Shine-Dalgarno sequence (T7 gene 10)
5525-5572 Multiple cloning site
5573-6166 Mxe GyrA intein (N198A)
6197-6352 Chitin-binding domain
6375-6497 T7 transcription terminator
```

TXB1.seq.old  Length: 6503  March 17, 1998  11:14  Type: N
Check: 1445 ..

```
   1 AACTACGTCA GGTGGCACTT TTCGGGGAAA TGTGCGCGGA ACCCCTATTT
  51 GTTTATTTTT CTAAATACAT TCAAATATGT ATCCGCTCAT GAGACAATAA
 101 CCCTGATAAA TGCTTCAATA ATATTGAAAA AGGAAGAGTA TGAGTATTCA
 151 ACATTTCCGT GTCGCCCTTA TTCCCTTTTT TGCGGCATTT TGCCTTCCTG
 201 TTTTTGCTCA CCCAGAAACG CTGGTGAAAG TAAAAGATGC TGAAGATCAG
 251 TTGGGTGCAC GAGTGGGTTA CATCGAACTG GATCTCAACA GCGGTAAGAT
 301 CCTTGAGAGT TTTCGCCCCG AAGAACGTTC TCCAATGATG AGCACTTTTA
 351 AAGTTCTGCT ATGTGGCGCG GTATTATCCC GTGTTGACGC CGGGCAAGAG
 401 CAACTCGGTC GCCGCATACA CTATTCTCAG AATGACTTGG TTGAGTACTC
 451 ACCAGTCACA GAAAAGCATC TTACGGATGG CATGACAGTA AGAGAATTAT
 501 GCAGTGCTGC CATAACCATG AGTGATAACA CTGCGGCCAA CTTACTTCTG
 551 ACAACGATCG GAGGACCGAA GGAGCTAACC GCTTTTTTGC ACAACATGGG
 601 GGATCATGTA ACTCGCCTTG ATCGTTGGGA ACCGGAGCTG AATGAAGCCA
 651 TACCAAACGA CGAGCGTGAC ACCACGATGC CTGTAGCAAT GGCAACAACG
 701 TTGCGCAAAC TATTAACTGG CGAACTACTT ACTCTAGCTT CCCGGCAACA
 751 ATTAATAGAC TGGATGGAGG CGGATAAAGT TGCAGGACCA CTTCTGCGCT
 801 CGGCCCTTCC GGCTGGCTGG TTTATTGCTG ATAAATCTGG AGCCGGTGAG
 851 CGTGGGTCTC GCGGTATCAT TGCAGCACTG GGGCCAGATG GTAAGCCCTC
```

FIG. 5B

```
 901  CCGTATCGTA GTTATCTACA CGACGGGGAG TCAGGCAACT ATGGATGAAC
 951  GAAATAGACA GATCGCTGAG ATAGGTGCCT CACTGATTAA GCATTGGTAA
1001  CTGTCAGACC AAGTTTACTC ATATATACTT TAGATTGATT TACCCCGGTT
1051  GATAATCAGA AAAGCCCCAA AAACAGGAAG ATTGTATAAG CAAATATTTA
1101  AATTGTAAAC GTTAATATTT TGTTAAAATT CGCGTTAAAT TTTTGTTAAA
1151  TCAGCTCATT TTTTAACCAA TAGGCCGAAA TCGGCAAAAT CCCTTATAAA
1201  TCAAAAGAAT AGCCCGAGAT AGGGTTGAGT GTTGTTCCAG TTTGGAACAA
1251  GAGTCCACTA TTAAAGAACG TGGACTCCAA CGTCAAAGGG CGAAAAACCG
1301  TCTATCAGGG CGATGGCCCA CTACGTGAAC CATCACCCAA ATCAAGTTTT
1351  TTGGGGTCGA GGTGCCGTAA AGCACTAAAT CGGAACCCTA AAGGGAGCCC
1401  CCGATTTAGA GCTTGACGGG GAAAGCCGGC GAACGTGGCG AGAAAGGAAG
1451  GGAAGAAAGC GAAAGGAGCG GGCGCTAGGG CGCTGGCAAG TGTAGCGGTC
1501  ACGCTGCGCG TAACCACCAC ACCCGCCGCG CTTAATGCGC CGCTACAGGG
1551  CGCGTAAAAG GATCTAGGTG AAGATCCTTT TTGATAATCT CATGACCAAA
1601  ATCCCTTAAC GTGAGTTTTC GTTCCACTGA GCGTCAGACC CCGTAGAAAA
1651  GATCAAAGGA TCTTCTTGAG ATCCTTTTTT TCTGCGCGTA ATCTGCTGCT
1701  TGCAAACAAA AAAACCACCG CTACCAGCGG TGGTTTGTTT GCCGGATCAA
1751  GAGCTACCAA CTCTTTTTCC GAAGGTAACT GGCTTCAGCA GAGCGCAGAT
1801  ACCAAATACT GTCCTTCTAG TGTAGCCGTA GTTAGGCCAC CACTTCAAGA
1851  ACTCTGTAGC ACCGCCTACA TACCTCGCTC TGCTAATCCT GTTACCAGTG
1901  GCTGCTGCCA GTGGCGATAA GTCGTGTCTT ACCGGGTTGG ACTCAAGACG
1951  ATAGTTACCG GATAAGGCGC AGCGGTCGGG CTGAACGGGG GGTTCGTGCA
2001  CACAGCCCAG CTTGGAGCGA ACGACCTACA CCGAACTGAG ATACCTACAG
2051  CGTGAGCTAT GAGAAAGCGC CACGCTTCCC GAAGGGAGAA AGGCGGACAG
2101  GTATCCGGTA AGCGGCAGGG TCGGAACAGG AGAGCGTACG AGGGAGCTTC
2151  CAGGGGGAAA CGCCTGGTAT CTTTATAGTC CTGTCGGGTT TCGCCACCTC
2201  TGACTTGAGC GTCGATTTTT GTGATGCTCG TCAGGGGGGC GGAGCCTATG
2251  GAAAAACGCC AGCAACGCGG CCTTTTTACG GTTCCTGGCC TTTTGCTGGC
2301  CTTTTGCTCA CATGTTCTTT CCTGCGTTAT CCCCTGATTC TGTGGATAAC
```

FIG. 5C

```
2351  CGTATTACCG CCTTTGAGTG AGCTGATACC GCTCGCCGCA GCCGAACGAC
2401  CGAGCGCAGC GAGTCAGTGA GCGAGGAAGC TATGGTGCAC TCTCAGTACA
2451  ATCTGCTCTG ATGCCGCATA GTTAAGCCAG TATACACTCC GCTATCGCTA
2501  CGTGACTGGG TCATGGCTGC GCCCCGACAC CCGCCAACAC CCGCTGACGC
2551  GCCCTGACGG GCTTGTCTGC TCCCGGCATC CGCTTACAGA CAAGCTGTGA
2601  CCGTCTCCGG GAGCTGCATG TGTCAGAGGT TTTCACCGTC ATCACCGAAA
2651  CGCGCGAGGC AGCTGCGGTA AAGCTCATCA GCGTGGTCGT GCAGCGATTC
2701  ACAGATGTCT GCCTGTTCAT CCGCGTCCAG CTCGTTGAGT TTCTCCAGAA
2751  GCGTTAATGT CTGGCTTCTG ATAAAGCGGG CCATGTTAAG GGCGGTTTTT
2801  TCCTGTTTGG TCACTTGATG CCTCCGTGTA AGGGGGAATT TCTGTTCATG
2851  GGGGTAATGA TACCGATGAA ACGAGAGAGG ATGCTCACGA TACGGGTTAC
2901  TGATGATGAA CATGCCCGGT TACTGGAACG TTGTGAGGGT AAACAACTGG
2951  CGGTATGGAT GCGGCGGGAC CAGAGAAAAA TCACTCAGGG TCAATGCCag
3001  ccgaACGCCA GCAAGACGTA GCCCAGCGCG TCGGCCGCCA TGCCGGCGAT
3051  AATGGCCTGC TTCTCGCCGA AACGTTTGGT GGCGGGACCA GTGACGAAGG
3101  CTTGAGCGAG GGCGTGCAAG ATTCCGAATA CCGCAAGCGA CAGGCCGATC
3151  ATCGTCGCGC TCCAGCGAAA GCGGTCCTCG CCGAAAATGA CCCAGAGCGC
3201  TGCCGGCACC TGTCCTACGA GTTGCATGAT AAAGAAGACA GTCATAAGTG
3251  CGGCGACGAT AGTCATGCCC CGCGCCCACC GGAAGGAGCT GACTGGGTTG
3301  AAGGCTCTCA AGGGCATCGG TCGAGATCCC GGTGCCTAAT GAGTGAGCTA
3351  ACTTACATTA ATTGCGTTGC GCTCACTGCC CGCTTTCCAG TCGGGAAACC
3401  TGTCGTGCCA GCTGCATTAA TGAATCGGCC AACGCGCGGG GAGAGGCGGT
3451  TTGCGTATTG GGCGCCAGGG TGGTTTTTCT TTTCACCAGT GAGACGGGCA
3501  ACAGCTGATT GCCCTTCACC GCCTGGCCCT GAGAGAGTTG CAGCAAGCGG
3551  TCCACGCTGG TTTGCCCCAG CAGGCGAAAA TCCTGTTTGA TGGTGGTTAA
3601  CGGCGGGATA TAACATGAGC TGTCTTCGGT ATCGTCGTAT CCCACTACCG
3651  AGATATCCGC ACCAACGCGC AGCCCGGACT CGGTAATGGC GCGCATTGCG
3701  CCCAGCGCCA TCTGATCGTT GGCAACCAGC ATCGCAGTGG GAACGATGCC
3751  CTCATTCAGC ATTTGCATGG TTTGTTGAAA ACCGGACATG GCACTCCAGT
```

FIG. 5D

```
3801  CGCCTTCCCG TTCCGCTATC GGCTGAATTT GATTGCGAGT GAGATATTTA
3851  TGCCAGCCAG CCAGACGCAG ACGCGCCGAG ACAGAACTTA ATGGGCCCGC
3901  TAACAGCGCG ATTTGCTGGT GACCCAATGC GACCAGATGC TCCACGCCCA
3951  GTCGCGTACC GTCTTCATGG GAGAAAATAA TACTGTTGAT GGGTGTCTGG
4001  TCAGAGACAT CAAGAAATAA CGCCGGAACA TTAGTGCAGG CAGCTTCCAC
4051  AGCAATGGCA TCCTGGTCAT CCAGCGGATA GTTAATGATC AGCCCACTGA
4101  CGCGTTGCGC GAGAAGATTG TGCACCGCCG CTTTACAGGC TTCGACGCCG
4151  CTTCGTTCTA CCATCGACAC CACCACGCTG GCACCCAGTT GATCGGCGCG
4201  AGATTTAATC GCCGCGACAA TTTGCGACGG CGCGTGCAGG GCCAGACTGG
4251  AGGTGGCAAC GCCAATCAGC AACGACTGTT TGCCCGCCAG TTGTTGTGCC
4301  ACGCGGTTGG GAATGTAATT CAGCTCCGCC ATCGCCGCTT CCACTTTTTC
4351  CCGCGTTTTC GCAGAAACGT GGCTGGCCTG GTTCACCACG CGGGAAACGG
4401  TCTGATAAGA GACACCGGCA TACTCTGCGA CATCGTATAA CGTTACTGGT
4451  TTCACATTCA CCACCCTGAA TTGACTCTCT TCCGGGCGCT ATCATGCCAT
4501  ACCGCGAAAG GTTTTGCGCC ATTCGATGGT GTCCCGGATC TCGACGCTCT
4551  CCCTTATGCG ACTCCTGCAT TAGGAAGCAG CCCAGTAGTA GGTTGAGGCC
4601  GTTGAGCACC GCCGCCGCAA GGAATGGTGC ATGCCGCCCT TTCGTCTTCA
4651  AGAATTAATT CCCAATTCCA GGCATCAAAT AAAACGAAAG CTCAGTCGA
4701  AAGACTGGGC CTTTCGTTTT ATCTGTTGTT TGTCGGTGAA CGCTCTCCTG
4751  AGTAGGACAA ATCCGCCGGG AGCGGATTTG AACGTTGCGA AGCAACGGCC
4801  CGGAGGGTGG CGGGCAGGAC GCCCGCCATA AACTGCCAGG AATTAATTCC
4851  AGGCATCAAA TAAAACGAAA GGCTCAGTCG AAAGACTGGG CCTTTCGTTT
4901  TATCTGTTGT TGTCGGTGA ACGCTCTCCT GAGTAGGACA AATCCGCCGG
4951  GAGCGGATTT GAACGTTGCG AAGCAACGCC CGGAGGGTG GCGGGCAGGA
5001  CGCCCGCCAT AAACTGCCAG GAATTAATTC CAGGCATCAA ATAAAACGAA
5051  AGGCTCAGTC GAAAGACTGG GCCTTTCGTT TTATCTGTTG TTTGTCGGTG
5101  AACGCTCTCC TGAGTAGGAC AAATCCGCCG GGAGCGGATT TGAACGTTGC
5151  GAAGCAACGG CCCGGAGGGT GGCGGGCAGG ACGCCCGCCA TAAACTGCCA
5201  GGAATTAATT CCAGGCATCA AATAAAACGA AAGGCTCAGT CGAAAGACTG
```

FIG. 5E

```
5251  GGCCTTTCGT TTTATCTGTT GTTTGTCGGT GAACGCTCTC CTGAGTAGGA
5301  CAAATCCGCC GGGAGCGGAT TTGAACGTTG CGAAGCAACG GCCCGGAGGG
5351  TGGCGGGCAG GACGCCCGCC ATAAACTGCC AGGAATTGGG GATCGGAATT
5401  AATTCCCGGT TTAAACCGGG GATCTCGATC CCGCGAAATT AATACGACTC
5451  ACTATAGGGG AATTGTGAGC GGATAACAAT TCCCCTCTAG AAATAATTTT
5501  GTTTAACTTT AAGAAGGAGA TATAcatatg gctagctcgc gagtcgacgg
5551  cggccgcctc gagggctctt ccTGCATCAC GGGAGATGCA CTAGTTGCCC
5601  TACCCGAGGG CGAGTCGGTA CGCATCGCCG ACATCGTGCC GGGTGCGCGG
5651  CCCAACAGTG ACAACGCCAT CGACCTGAAA GTCCTTGACC GGCATGGCAA
5701  TCCCGTGCTC GCCGACCGGC TGTTCCACTC CGGCGAGCAT CCGGTGTACA
5751  CGGTGCGTAC GGTCGAAGGT CTGCGTGTGA CGGGCACCGC GAACCACCCG
5801  TTGTTGTGTT TGGTCGACGT CGCCGGGGTG CCGACCCTGC TGTGGAAGCT
5851  GATCGACGAA ATCAAGCCGG GCGATTACGC GGTGATTCAA CGCAGCGCAT
5901  TCAGCGTCGA CTGTGCAGGT TTTGCCCGCG AAAACCCGA ATTTGCGCCC
5951  ACAACCTACA CAGTCGGCGT CCCTGGACTG GTGCGTTTCT TGGAAGCACA
6001  CCACCGAGAC CCGGACGCCC AAGCTATCGC CGACGAGCTG ACCGACGGGC
6051  GGTTCTACTA CGCGAAAGTC GCCAGTGTCA CCGACGCCGG CGTGCAGCCG
6101  GTGTATAGCC TTCGTGTCGA CACGGCAGAC CACGCGTTTA TCACGAACGG
6151  GTTCGTCAGC CACGCTACTG GCCTCACCGG TCTGAACTCA GGCCTCACGA
6201  CAAATCCTGG TGTATCCGCT TGGCAGGTCA ACACAGCTTA TACTGCGGGA
6251  CAATTGGTCA CATATAACGG CAAGACGTAT AAATGTTTGC AGCCCCACAC
6301  CTCCTTGGCA GGATGGGAAC CATCCAACGT TCCTGCCTTG TGGCAGCTTC
6351  AATGActgca ggaaggGGAT CCGGCTGCTA ACAAAGCCCG AAAGGAAGCT
6401  GAGTTGGCTG CTGCCACCGC TGAGCAATAA CTAGCATAAC CCCTTGGGGC
6451  CTCTAAACGG GTCTTGAGGG GTTTTTTGCT GAAAGGAGGA ACTATATCCG
6501  GAT
```

WESTERN BLOTS OF PROTEINS LIGATED TO A BIOTINYLATED PEPTIDE

INTEIN MEDIATED PEPTIDE LIGATION

This Application gains priority from U.S. Provisional Application Ser. No. 60/102,413 filed Sep. 30, 1998.

BACKGROUND OF THE INVENTION

Genetic engineering is a powerful approach to the manipulation of proteins. However, genetic methodologies are constrained by the use of only naturally coded amino acids. Furthermore, cytotoxic proteins are difficult to obtain by expression and isolation from a living source, since the expression of the toxic protein can result in death of the host.

To some extent, protocols have been developed to circumvent these problems, for example, total chemical synthesis (Kent, S. B. (1988) *Ann. Rev. Biochem.* 57:957–989), use of misacylated tRNAs (Noren, et al., (1989) *Science* 244:182–188), and semi-synthetic techniques (reviewed in Offord, R. (1987) *Protein Eng.* 1:151–157; Roy. et al. (1994) *Methods in Enzymol.* 231:194–215; Wallace, C. J. (1993) *FASEB* 7:505–515). However, all of these procedures are limited by either the size of the fragment which can be generated or by low reaction yield.

It would therefore be desirable to develop a high-yield, semi-synthetic technique to allow in vitro fusion of a synthetic protein or peptide fragment to an expressed protein without limitation as to the size of the fused fragments.

Likewise, in order to produce cytotoxic proteins, it would be desirable to develop a method of fusing a synthetic fragment, in vitro, to an inactive, expressed protein, so as to restore protein activity post-production from the host.

The modified Sce VMA intein has been used to generate thioester-tagged proteins for use in ligation (Example 19, U.S. Ser. No. 08/811,492, filed Jun. 16, 1997; Chong, (1996) *J. Biol. Chem.*, 271(36):22159–22168; Chong, (1997) *Gene*, 192:271–281; and Muir, et al. (1998) *Proc. Natl. Acad. Sci USA* 95:6705–6710).

Some disadvantages have been low yields due to poor cleavage of the Sce VMA intein with thiol-reagents that are optimum for ligation, the need for large peptide quantities due to on-column reactions, the use of odoriferous reagents, and/or low protein yields due to the use of a large, eukaryotic intein.

SUMMARY OF THE INVENTION

In accordance with the present invention, there is provided a method for producing a semi-synthetic fusion protein in vitro, comprising the steps of producing a target protein fused to a protein splicing element (an intein) and selectively cleaving the fusion and ligating a synthetic protein or peptide at the C-terminal thioester of the target protein, which overcome many of the disadvantages and problems noted above. The term "protein splicing element" according to U.S. Pat. No. 5,834,247 ('247) is intended to include native and modified protein splicing elements, where modification of the protein splicing element may include: a mutation of one or more amino acid residues at the splice junction; or derivatives that are exemplified by the introduction of a protein phosphorylation, glycosylation or photolysis activation site at the sequence surrounding the mutation, or chemical modification of splice junction residues. Specifically, the present invention has higher yields due to better thiol-induced cleavage with thiol reagents which have been optimized for the ligation reaction. Off-column ligation allows for sample concentration as well as the use of less peptide. In a particularly preferred embodiment, thiol reagents such as 2-mercaptoethanesulfonic acid (MESNA), which is an odorless thiol-reagent, is used for cleavage and ligation along with the Mxe Gyr A intein, which is from a bacterial source and often expresses better in bacterial cells. Furthermore, the present invention allows peptides to be directly ligated to the thioester bond formed between an intein and the target protein. The present invention also provides a method for producing a cytotoxic protein, comprising the steps of producing a truncated, inactive form of the protein in vivo which is fused to a protein splicing element, and selectively cleaving the fusion and ligating a synthetic protein or peptide at a C-terminal thioester of the target protein to restore the activity of the native cytotoxic protein. Recombinant vectors for producing such cleavable fusion proteins are also provided.

BRIEF DESCRIPTION OF THE DRAWINGS

FIG. 5 is the DNA sequence of pTXB1 (SEQ ID NO:5).

DETAILED DESCRIPTION OF THE INVENTION

The ligation methods of the present invention are based on the discovery that a cysteine or peptide fragment containing an N-terminal cysteine may be fused, in vitro, to a bacterially expressed protein produced by thiol-induced cleavage of an intein (U.S. Pat. No. 5,496,714; Example 19 of U.S. Ser. No. 08/811,492 filed Jun. 16, 1997; Chong, et al., (1996) supra and Chong, et al., (1997) supra.

The ligation procedure disclosed herein utilizes a protein splicing element, an intein (Perler, et al., (1994) *Nucleic Acids Res.* 22:1125–1127) to precisely create a thioester at the C-terminus of an expressed protein. This reactive thioester could be present between the target protein and intein or generated by the addition of a thiol reagent. Previously the generation of such a thioester was described using an intein (CIVPS) that was modified to undergo thiol inducible cleavage at its N-terminal junction in the presence of the thiol reagent dithiothreitol (DTT) (Chong, et al. (1997) supra; Comb, et.al. U.S. Pat. No. 5,496,714). This C-terminal thioester was previously used in a 'native chemical ligation' type reaction (Dawson, et al., (1994) *Science* 266:776–779) to fuse $^{35}$S-cysteine or a peptide fragment containing an N-terminal cysteine to a bacterially expressed protein (Example 19, Comb, et.al. U.S. Pat. No. 5,834,247, Chong (1996) supra and Chong (1997) supra.

Figure 1:
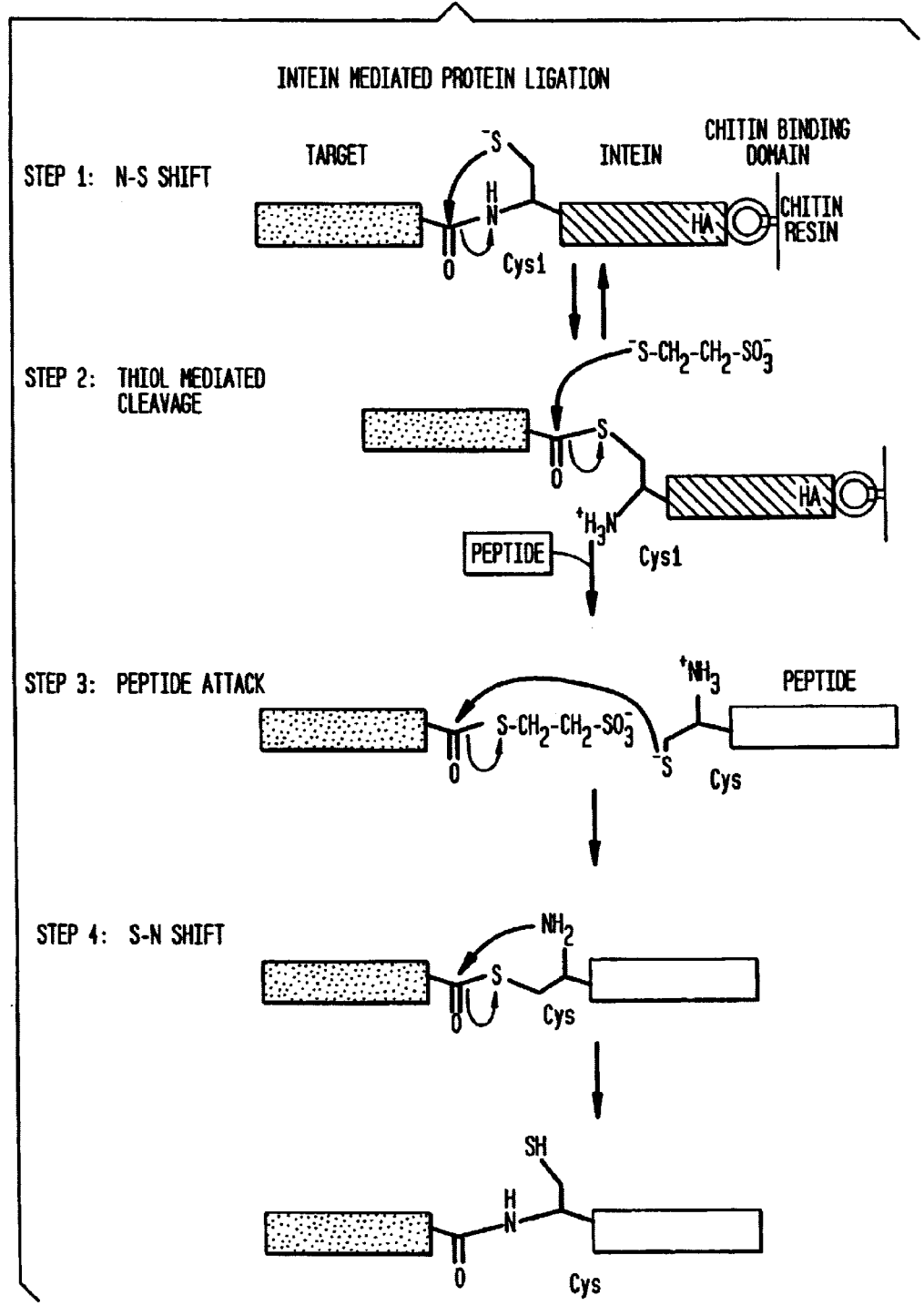
FIG. 1 is a flow diagram depicting the chemical reactions which enable intein-mediated peptide ligation. The thioester generated at the C-terminus of the target protein during IMPACT™ purification was used in a 'native chemical ligation' reaction. This allowed the ligation of a synthetic peptide to a bacterially expressed protein. A typical ligation reaction involved the expression of the target protein-intein-CBD fusion followed by binding to a chitin resin. A thiol reagent induced cleavage of the intein. The target was eluted from the chitin resin and a synthetic peptide was added. The ligation reaction proceeded overnight.

The ligation method of the instant invention begins with the purification of the thioester-tagged target protein using an intein as described (Chong, et.al. (1997) supra). The direct ligation method of the instant invention begins with the isolation of a precursor composed of the target protein-intein-CBD. In one preferred embodiment, the host cell is bacterial. In other embodiments the host cell may be yeast, insect, or mammalian. A cysteine thiol at the N-terminus of a synthetic peptide nucleophilicly attacks a C-terminal thioester present on the freshly isolated target protein or directly attacks the thioester present between the target protein and intein. This initially generates a thioester between the two reactants which spontaneously rearranges into a native peptide bond (FIG. 1).

In order to optimize the ligation efficiency so that greater than 90% of the bacterially expressed target protein can be fused to the synthetic peptide or protein, specific thiol reagents and inteins are screened. In a preferred embodiment, the intein may be any CIVPS, such as Sce VMA, Mxe GyrA or derivatives of mutants thereof, and the thiol reagent is 2-mercapto-ethanesulfonic acid, thiophenol, DTT, or 3-mercaptopropionic acid (Comb, et al., U.S. Pat. Nos. 5,496,714; 5,834,247).

Figure 2:
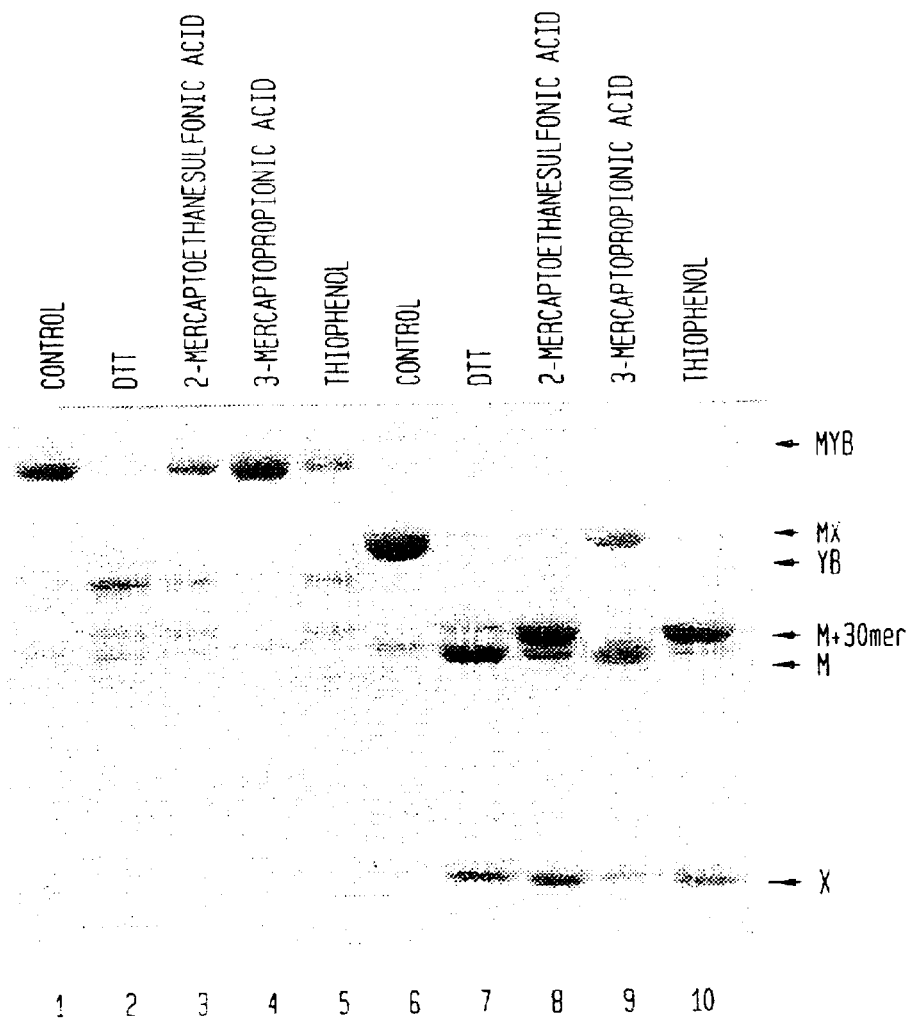
FIG. 2 is a gel depicting the results of cleavage and ligation reactions using various thiols. Cleavage and ligation reactions with different thiols visualized on 10–20% Tricine gels. MYB (a fusion protein of maltose binding protein-Sce VMA intein (N454A)-chitin binding domain) and MXB (a fusion protein of maltose binding protein-Mxe GyrA (N198A) intein-chitin binding domain) were incubated overnight at 4° C. with various thiols (50 mM) in 150 mM Tris, 100 mM NaCl, pH 8 in the presence of a 30 amino acid peptide with an N-terminal cysteine. The peptide ligates to the C-terminus of MBP. Lanes 1–5 ligation with MYB. Lane 1 no thiol. Lane 2 dithiothreitol. Lane 3 2-mercaptoethanesulfonic acid. Lane 4 3-mercaptopropionic acid. Lane 5 thiophenol. Lanes 6–10 ligation with MXB. Lane 6 no thiol. Lane 7 dithiothreitol. Lane 8 2-mercaptoethanesulfonic acid. Lane 9 3-mercaptopropionic acid. Lane 10 thiophenol.

In one particularly preferred embodiment, an intein whose protein splicing activity has been blocked by mutation is utilized. The mutant must, however, retain the ability to undergo the N-S shift, thus allowing thioester formation between itself and an N-terminal protein. This thioester can then be nucleophilicly attacked by a thiol reagent or by the N-terminal cysteine of a peptide sequence. For example, by mutating the C-terminal asparagine (asn 198) of an intein from the GyrA gene of *Mycobacterium xenopi* (Telenti, et al., (1997) *J Bacteriol* 179:6378–6382) to an alanine created a thiol inducible cleavage element. This modified intein cleaved well with thiol reagents that were optimal for the ligation reaction, such as MESNA and thiophenol. Furthermore, optimal thiol reagent and intein combinations can be determined by incubating a precursor protein containing the intein of interest with a wide variety of thiol reagents followed by determination of the extent of cleavage of the precursor protein (FIG. 2).

The use of such intein and specific thiol reagents leads to optimal yields and high ligation efficiencies; typically greater than 90% of the N-terminal ligation fragment can be modified.

The ligation methods of the present invention expand the ability to incorporate non-coded amino acids into large protein sequences by generating a synthetic peptide fragment with fluorescent probes, spin labels, affinity tags, radiolabels, or antigenic determinants and ligating this to an in vivo expressed protein isolated using a modified intein.

Furthermore, this procedure allows the isolation of cytotoxic proteins by purifying an inactive truncated precursor from a host source, for example bacteria, and generating an active protein or enzyme after the ligation of a synthetic peptide. For example, restriction endonucleases which have not successfully been cloned by traditional methods may be produced in accordance with the present invention.

Figure 3:
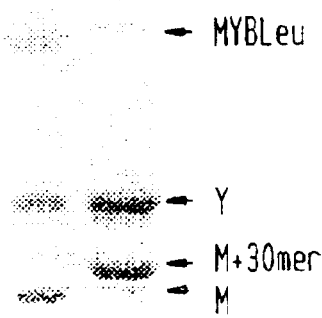
FIG. 3 is a gel depicting direct ligation of a peptide to the thioester formed between the Sce VMA intein and maltose binding protein. SDS-PAGE of direct ligation reaction with a 10–20% Tricine gel. Lane 1: a precursor protein (MYBleu) consisting of maltose binding protein-Sce VMA1 intein-chitin binding domain was heated to >95° C. for 5 minutes in a buffer of 50 mM Trizma base, pH 8.5 containing 100 mM NaCl, 1% SDS, and mM tris-(2-carboxyethyl) phosphine (TCEP) followed by overnight incubation at room temperature. The precursor (MYBleu) is visible along with the Sce VMA1 intein (Y) and maltose binding protein (M), which are cleavage products. Lane 2: the precursor protein was subjected to the same conditions as described in Lane 1 except that the 30 amino acid peptide (1 mM) was added. The precursor (MYB) and cleavage products (Y and M) are visible along with the ligation product (M+30mer) formed when the 30 amino acid peptide fuses to maltose binding protein.

Also, the direct ligation procedure allows the ligation of a protein or peptide sequence to another protein or peptide sequence without the use of exogenous thiol reagents. Direct ligation relies on the nucleophilic attack of the N-terminal amino acid of one peptide on the thioester formed between a target protein and an intein (FIG. 3).

In summary, a fusion protein can be created using the methods of the present invention that possesses unique properties which, currently, can not be generated genetically.

The Examples presented below are only intended as specific preferred embodiments of the present invention and are not intended to limit the scope of the invention. The present invention encompasses modifications and variations of the methods taught herein which would be obvious to one of ordinary skill in the art.

The references cited above and below are herein incorporated by reference.

EXAMPLE I

Creation of Vectors pTXB1 and pTXB2 for Ligation

Asparagine 198 of the Mxe GyrA intein (Telenti, et al., (1997) *J Bacteriol.* 179:6378–6382) was mutated to alanine by linker insertion into the XmnI and PstI sites of pmxeMI-PTyrXmnSPdel to create pMXP1. The XmnI site was originally introduced into the unmodified Mxe GyrA intein sequence by silent mutagenesis. The PstI site was a unique site in the plasmid. The linker was composed of mxe#3

(5'-GGTTCGTCAGCCACGCTACTGGCCTCACCGGT TGATAGCTGCA-3') (SEQ ID NO:1) and mxe#4 (5'-GCTATCAACCGGTGAGGCCAGTAGCGTGGCTGAC GAACC-3') (SEQ ID NO:2).

Into pMXP1 another linker composed of mxe#1 (5'-TCGAATCTAGACATATGGCCATGGGTGGCGGCCGC CTCGAGGGCTCTTCCTGCATCACGGGAGATGCA-3') (SEQ ID NO:3) and mxe#2 (5'-CTAGTGCATCTCCCGT GATGCAGGAAGAGCCCTCGAGGCGHGCCGCCACC CATGGCCATATGTCTAGAT-3') (SEQ ID NO:4) was inserted into the XhoI and SpeI sites to introduce a multiple cloning site (Xbal-Ndel-Ncol-Notl-Xhol-Sapl) before the Mxe GyrA intein (pMXP2).

Figure 4:
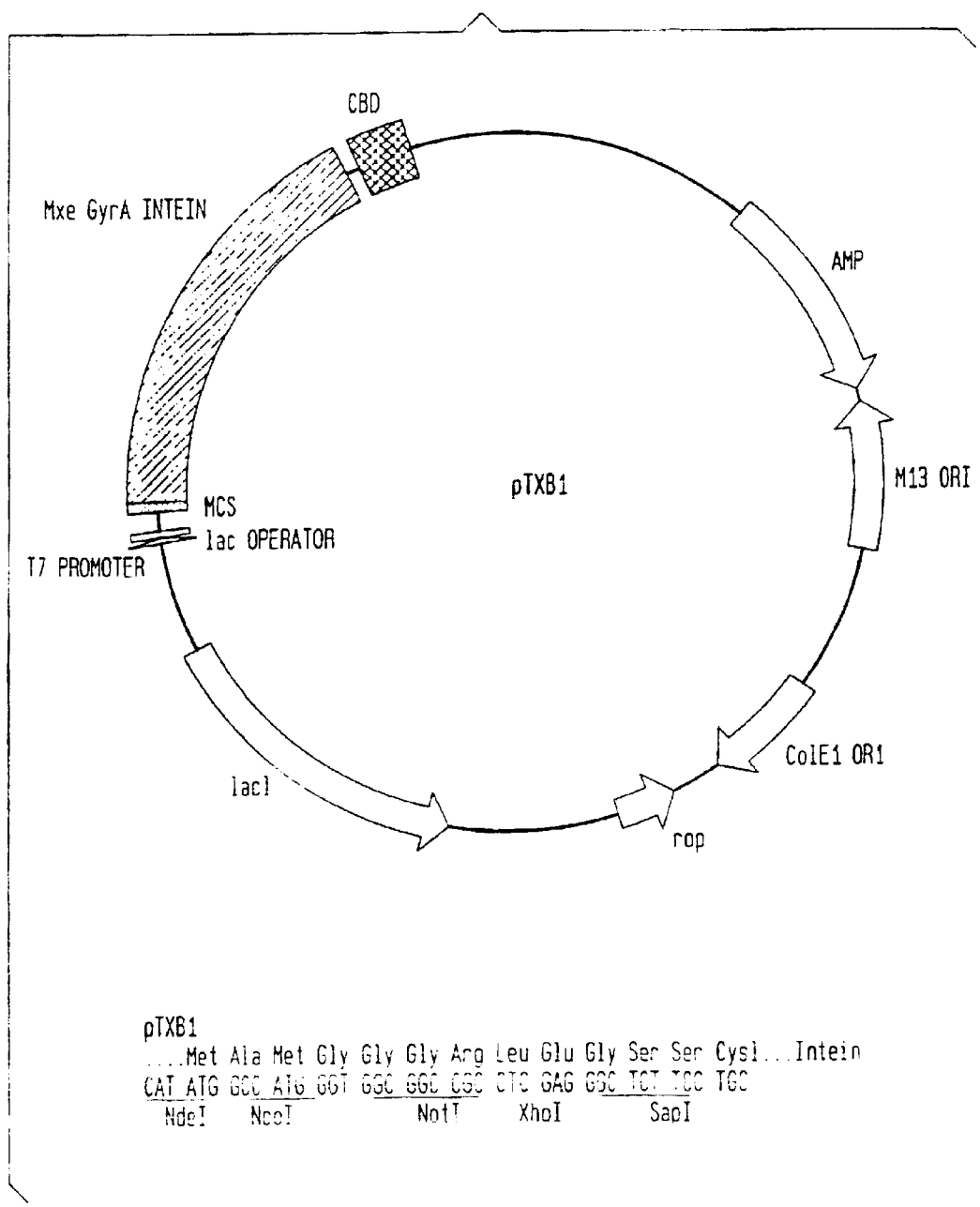
FIG. 4 is a diagram depicting the pTXB1 expression vector of Example I (SEQ ID NO:7 and SEQ ID NO:8).

The 0.6 kilobase NotI to AgeI fragment of pMXP2 was ligated into the same sites in pTYB1 (IMPACT kit, New England Biolabs, Beverly, Mass.) and the NcoI to AgeI fragment of pMXP2 was cloned into pTYB3 (IMPACT kit, New England Biolabs, Beverly, Mass.) to create plasmids pTXB1 (see FIGS. 4 and 5) (SEQ ID NO:5) and pTXB2, respectively. These vectors have a multiple cloning site upstream of the modified Mxe GyrA intein-chitin binding domain fusion. This allows the insertion of a target gene of interest inframe with the intein and chitin binding domain (CBD).

Creation of Vectors pMYBleu for Ligation pMYBleu was as described in Chong, et al., (1998), *J. Biol. Chem.* 273:10567–10577. This vector consisted of maltose binding protein upstream of the Sce VMA intein-chitin binding domain. A leucine is present at the −1 position instead of the native residue (which is a glycine).

Purification of Thioester-Tagged Proteins

Protein purification was as described using the Sce VMA intein (Chong, et.al., (1997) *Gene* 192:271–281) with slight modification. ER2566 cells (IMPACT T7 instruction manual from New England Biolabs, Beverly, Mass.) containing the pTXB vector with the appropriate insert were grown to an $OD_{600}$ of 0.5–0.6 at 37° C. at which point they were induced with 0.5 mM IPTG overnight at 15° C. Cells were harvested by centrifugation and lysed by sonication (performed on ice). The three part fusion protein was bound to chitin beads (10 mL bed volume, FIG. 6, lanes 1 and 2) equilibrated in Buffer A (50 mM Tris, pH 7.4, and 500 mM NaCl), and washed with 10 column volumes of Buffer A to remove unbound material.

Figure 6:
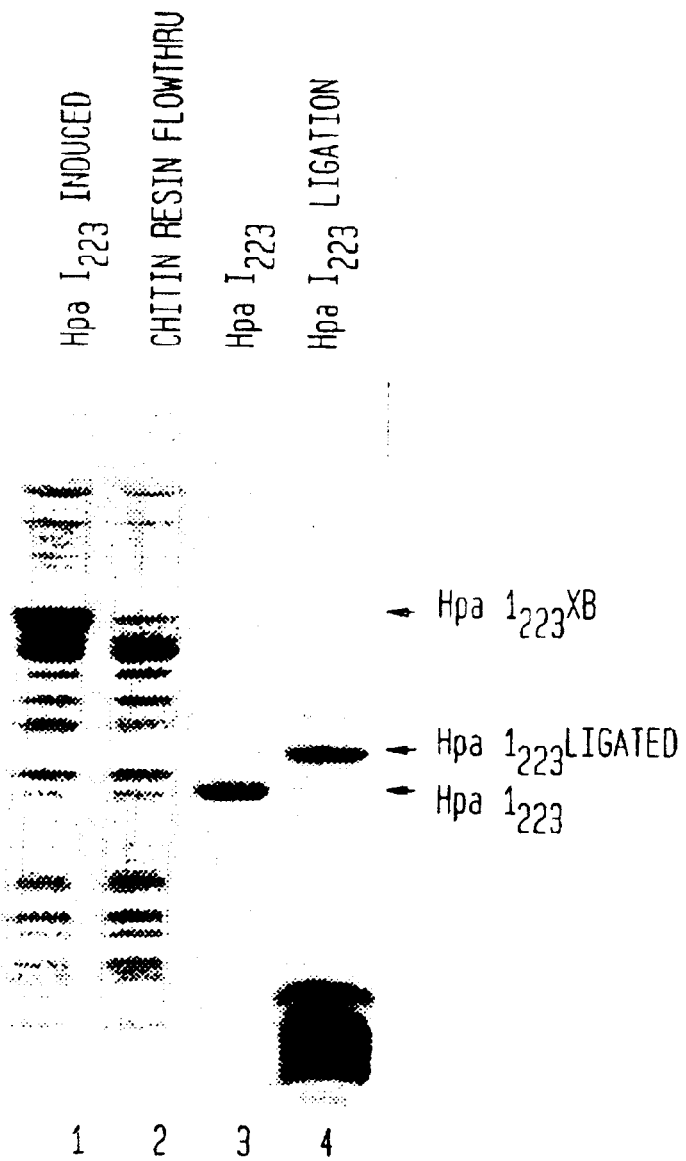
FIG. 6 is a gel depicting the results of the HpaI protein ligation reaction. Protein ligation reactions examined on 10–20% Tricine gels. Lane 1: clarified cells extract after IPTG (0.5 mM) induction of ER2566 cells containing the pTXB2-HpaI plasmid. The fusion protein of HpaI$_{223}$-Mxe GyrA-intein-CBD (52 kDa) is visible. Lane 2: cell extract as in Lane 1 after passage over a chitin column, which results in the binding of the fusion protein. Lane 3: HpaI$_{223}$ (25.7 kDa) after cleavage from the fusion protein by addition of MESNA. Lane 4: ligation product of HpaI$_{223}$ (0.2 mg/mL) with 1 mM of a 31 amino acid peptide (ligation product 29.6 kDa), representing the residues necessary to generate full length HpaI, after overnight incubation at 4° C. Lane 5: full length HpaI from a recombinant source (29.6 kDa) containing BSA (66 kDa) and two impurities.

Cleavage was initiated using a buffer of 50 mM 2-mercaptoethanesulfonic acid (MESNA), 50 mM Tris, pH 8.0 and 100 mM NaCl. Other thiol reagents were also used at other times, such as thiophenol, dithiothreitol, and/or 3-mercaptopropionic acid. After overnight incubation at from 4–25° C. protein was eluted from the column (FIG. 6 lane 3). This protein contained a thioester at the C-terminus.

Purification of MYB, MYBleu and MXB

Full length precursor proteins consisting of maltose binding protein-Sce VMA intein (N454A)-chitin binding domain (MYB) and maltose binding protein-Mxe GyrA (N198A) intein-chitin binding domain (MXB) were purified after induction and sonication, as described above, by applying the sonicated sample to a 10 mL column of amylose resin (New England Biolabs. Beverly, Mass.). Unbound proteins were washed from the column with 10 column volumes of Buffer A (see purification of thioester-tagged proteins) Bound proteins were eluted with a buffer of 50 mM Tris, pH 8, containing 100 mM NaCl and 10 mM maltose. Fractions were collected and protein concentrations were determined using the Bio-Rad Protein Assay (Herrules, Calif.).

Peptide Synthesis

Peptides for subsequent ligation reactions were synthesized on an ABI model 433A peptide synthesizer utilizing FastMoc™ chemistry (Fields, et al., (1991) *Pept Res* 4, 95–101) at a 0.085 mmol scale. Preloaded HMP (p-hydroxymethylphenoxymethyl) polystyrene resins (Applied Biosystems, Foster City, Calif.) functionalized at 0.5 mmol/g was used in conjunction with Fmoc/NMP chemistry utilizing HBTU amino acid activation (Dourtoglou, et al., (1984) *Synthesis* 572–574; Knorr, et al., (1989) *Tetrahedron Lett* 30, 1927–1930). Fmoc amino acids were purchased from Applied Biosystems (Foster City, Calif.).

Synthesis proceeded with a single coupling during each cycle. Peptide cleavage from the resin and simultaneous removal of side chain protecting groups was facilitated by the addition of cleavage mixture (Perkin Elmer, Norwalk, Conn.) consisting of 0.75 g phenol, 0.25 mL 1,2-ethanedithiol, 0.5 mL deionized $H_2O$, and 10 mL TFA. The resin was flushed with nitrogen and gently stirred at room temperature for 3 hours. Following filtration and precipitation into cold (0° C.) methyl-t-butyl ether, the precipitate in the ether fraction was collected by centrifugation. The peptide precipitate was vacuum dried and analyzed by mass spectrometry using a Perceptive Biosystems (Framingham, Mass.) MALDI-TOF mass spectrometer.

Final purification was by HPLC using a Waters HPLC system with a Lambda-Max Model 481 Multiwavelength detector (set at 214 nm). 500 series pumps and automated gradient controller with a Vydac semi-preparative C18 column. Elution of the peptide was with a 60 minute linear gradient of 6–60% acetonitrile (v/v) in an aqueous solution of 0.1% TFA (v/v).

Protein Cleavage and Ligation Reactions

Cleavage of MYB and MXB: The precursor protein (1 mg/mL) was incubated overnight at 40° C. with or without a thiol reagent (50 mM) in 150 mM Tris, pH 8, containing 100 mM NaCl.

Ligation reactions with MYB and MXB: The precursor protein (1 mg/mL) was treated as described for cleavage except that a 30 amino acid peptide (1 mM final concentration. $NH_2$-CAYKTTQANKHIIVACEGNPYVPVHFDASV-COOH (SEQ ID NO:6) was also included in the reaction (FIG. 2).

Ligation reactions after purification of thioester-tagged proteins: Lyophilized peptides (New England Biolabs. Beverly, Mass.) were added (to 1 mM final concentration) directly to the thioester-tagged protein freshly isolated from the chitin column. The reaction was allowed to proceed overnight at from 4–25° C. In both ligation procedures the condensation of the reactants is visible on a 10–20% Tricine gel (FIG. 6). The ligation reaction was tested in conditions of 5–150 mM Tris or HEPES buffers, 50–1000 mM NaCl, 10 mM Maltose, and pH 6–11 and 0–6 M Urea.

Direct Ligation Reactions

MYBleu (1 mg/mL) was incubated in 6 M Urea or 1% SDS, pH 7.5–8.5, 50–200 mM NaCl, and 1 mM of a 30 amino acid peptide ($NH_2$CAYKTTQANKHIVVACEGNPYVPVHFDASV-COOH (SEQ ID NO:6)). The MYBleu was incubated for 0–180 minutes at either 4° C. or 100° C. prior to the addition of the 30 amino acid peptide. Ligation reactions proceeded overnight at either 4° C. or 25° C.

EXAMPLE II

Labeling a Target Protein: Maltose Binding Protein

Maltose binding protein (MBP, 42 kDa) was isolated as described in Example I above using the IMPACT procedure (IMPACT manual from New England Biolabs, Inc., Beverly, Mass.) in the presence of MESNA.

A biotinylated peptide possessing an N-terminal cysteine (CDPEK*DS-COOH (SEQ ID NO:9)), in which the biotin was attached to the ε-amino group of the lysine residue) was ligated to the freshly purified target protein as described above. Briefly, 4 μL of biotinylated peptide (10 mM) were mixed with a 36 μL aliquot of the freshly purified MBP sample. The mixture was incubated at 4° C. overnight.

Figure 7:
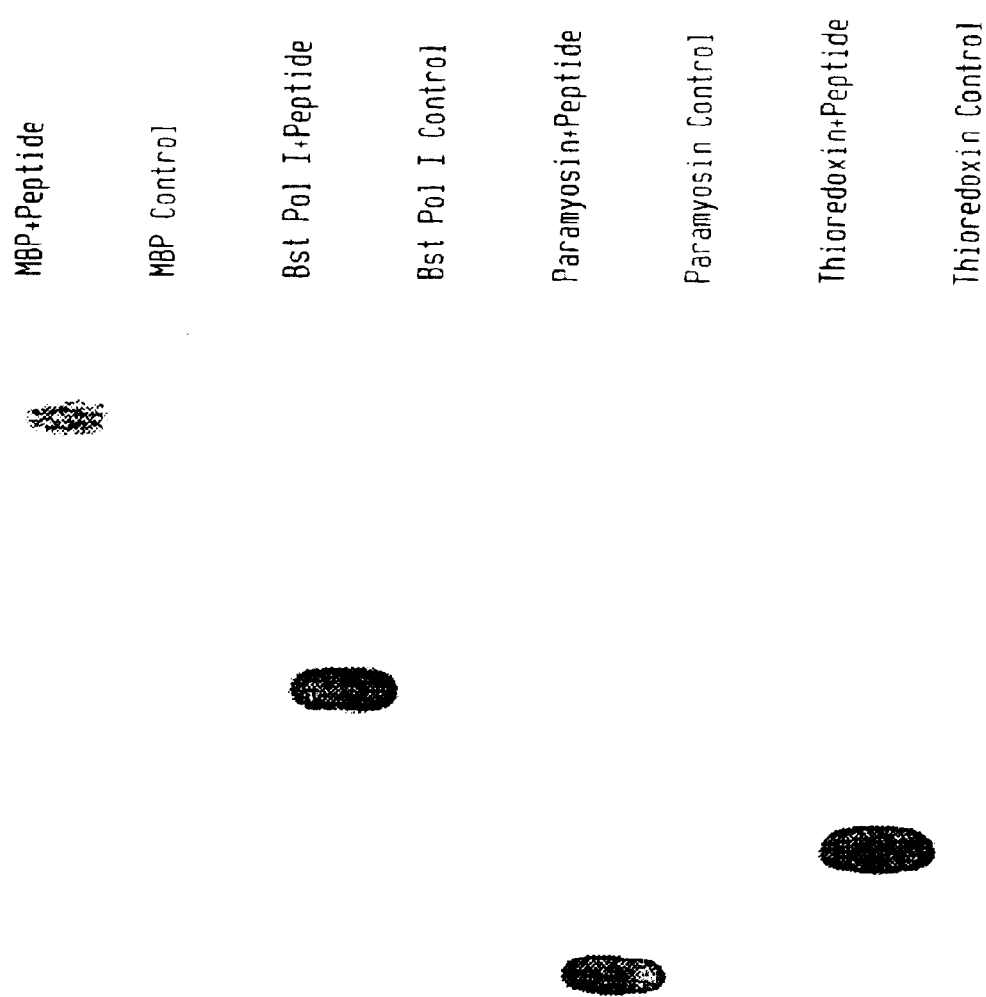
FIG. 7 is a western blot of various proteins ligated to a biotinylated peptide. Proteins Purified with the Mxe GyrA IMPACT™ derivative were ligated to a synthetic peptide which contained an antibody recognition sequence.

Western blots with alkaline phosphatase linked anti-biotin antibody detected the presence of the ligated product but not the unligated target protein (FIG. 7). The efficiency of the ligation is typically greater than 90% when MESNA is used for cleavage.

EXAMPLE III
Labeling a Target Protein: Bst DNA Polymerase I Large Fragment (Bst Pol 1)

Bst DNA Polymerase I large fragment (67 kDa) was isolated as described in Example I above using the IMPACT procedure (IMPACT manual from New England Biolabs, Inc., Beverly, Mass.) in the presence of MESNA.

A biotinylated peptide possessing an N-terminal cysteine (CDPEK*DS-COOH (SEQ ID NO:9)), in which the biotin was attached to the L-amino group of the lysine residue) was ligated to the freshly purified target protein as described. Briefly, 4 µL of biotinylated peptide (10 mM) were mixed with a 36 µL aliquot of the freshly purified Bst Pol 1 sample. The mixture was incubated at 4° C. overnight.

Western blots with alkaline phosphatase linked anti-biotin antibody detected the presence of the ligated product but not the unligated target protein (FIG. 7). The efficiency of the ligation is typically greater than 90% when MESNA is used for cleavage

EXAMPLE IV
Labeling a Target Protein: Paramyosin

Paramyosin (29 kDa) was isolated as described in Example I above using the IMPACT procedure (IMPACT manual from New England Biolabs, Inc., Beverly, Mass.) in the presence of MESNA.

A biotinylated peptide possessing an N-terminal cysteine (CDPEK*DS-COOH (SEQ ID NO:9)), in which the biotin was attached to the ε-amino group of the lysine residue) was ligated to the freshly purified target protein as described Briefly, 4 µL of biotinylated peptide (10 mM) were mixed with a 36 µL aliquot of the freshly purified paramyosin sample. The mixture was incubated at 4° C. overnight.

Western blots with alkaline phosphatase linked anti-biotin antibody detected the presence of the ligated product but not the unligated target protein (FIG. 7). The efficiency of the ligation is typically greater than 90% when MESNA is used for cleavage.

EXAMPLE V
Labeling a Target Protein: *E. coli* Thioredoxin

*E. Coli* thioredoxin (12 kDa) was isolated as described in Example I above using the IMPACT procedure (IMPACT manual from New England Biolabs, Inc., Beverly, Mass.) in the presence of MESNA.

A biotinylated peptide possessing an N-terminal cysteine (CDPEK*DS-COOH (SEQ ID NO:9)), in which the biotin was attached to the ε-amino group of the lysine residue) was ligated to the freshly purified target protein as described. Briefly, 4 µL of biotinylated peptide (10 mM) were mixed with a 36 µL aliquot of the freshly purified thioredoxin sample. The mixture was incubated at 4° C. overnight.

Western blots with alkaline phosphatase linked anti-biotin antibody detected the presence of the ligated product but not the unligated target protein (FIG. 7). The efficiency of the ligation is typically greater than 90% when MESNA is used for cleavage.

EXAMPLE VI
Isolation of a Cytotoxic Protein

The ligation procedure of Example I was applied to the isolation of a potentially cytotoxic protein. An endonuclease from *Haemophilus parainfluenzae* (Hpal; Ito, et al., (1992) *Nucleic Acids Res* 20:705–709) was generated by ligating an inactive truncated form of the enzyme expressed in *E. Coli* (ER2566 cells, New England Biolabs, Inc., Beverly, Mass.) with the missing amino acids that were synthesized chemically.

The first 223 amino acids of Hpal (full length Hpal is 254 amino acids) were fused in frame with the modified Mxe GyrA intein and the CBD. The 223 amino acid Hpal fragment was isolated as described for purification of thioester tagged proteins. The truncated Hpal displayed no detectable enzymatic activity.

A synthetic peptide representing the 31 amino acids needed to complete Hpal was ligated onto the 223 amino acid truncated form of Hpal by the method of Example I.

Enzymatic Assay for Hpal

The activity of the fused Hpal was determined by its ability to digest Lambda DNA (New England Biolabs, Beverly, Mass.). Serial dilutions of ligated or truncated Hpal, with the appropriate peptide added to 1 mM, were incubated with 1 µg of Lambda DNA for 1 hour at 37° C. in a buffer of 20 mM Tris-acetate, pH 7.9, 10 mM magnesium acetate, 50 mM potassium acetate, 1 mM dithiothreitol, and 170 µg/mL BSA (total volume 30 µL). Digestion reactions were visualized on 1% agarose gels permeated with ethidium bromide. One unit of Hpal was defined as the amount of enzyme necessary to digest 1 µg of Lambda DNA in one hour at 37° C.

The newly ligated Hpal had a specific activity of 0.5–1.5× $10^6$ units/mg which correlated well with the expected value of 1–2×$10^6$ units/mg for the full length enzyme.

What is claimed is:

1. A method for preparing a target protein with a carboxy-terminal thioester, comprising:
   (a) expressing a recombinant precursor protein in a host cell, the precursor protein comprising the target protein fused at its carboxy terminus to the amino terminus of an intein, the intein being selected from the group consisting of a native intein, an intein derivative, and a mutant intein, wherein the intein is optionally fused at its carboxy terminus to a binding protein domain; and,
   (b) contacting the expressed precursor protein with 2-mercaptoethanesulfonic acid to induce cleavage of the intein from the precursor protein;
thereby forming the target protein having the carboxy-terminal thioester.

2. The method according to claim 1, wherein the intein is selected from *Saccharomyces cerevisiae* Vma intein and *Mycobacterium xenopi* Gyr A intein.

3. The method according to claim 1, wherein the binding protein domain is a chitin binding domain.

4. The method according to claim 1, wherein the target protein is selected from a *Bacillus stearothermophilus* DNA polymerase I large fragment, thioredoxin or a cytotoxic protein.

5. The method according to claim 1, wherein the binding protein domain is selected from a maltose binding protein and paramyosin.

6. A method for expressing a recombinant protein precursor, comprising:
   (a) inserting a nucleic acid sequence encoding a target protein into a plasmid at a multiple cloning site located upstream of and in frame with a fusion gene encoding an intein and a binding protein domain, wherein
      (i) the intein is selected from the group consisting of a native intein, an intein derivative, or a mutant intein; and
      (ii) the multiple cloning site contains a linker having a nucleic acid sequence selected from the group consisting of SEQ ID NO:1; SEQ ID NO:2; SEQ ID NO:3; and SEQ ID NO:4; and
   (b) transforming a host cell with the plasmid and providing conditions suitable for expressing the recombinant precursor protein by the host cell;
whereby the recombinant protein precursor is expressed.

7. The method of claim 6, wherein the binding protein domain encoded by the fusion gene is a chitin binding protein.

8. The method according to claim 6, wherein the plasmid is a pTXB plasmid.

9. A method of modifying a target protein by ligating a chemically synthesized peptide or protein to the target protein in vitro, comprising:
   (a) expressing a recombinant precursor protein in a host cell, the precursor protein comprising the target protein fused at its carboxy terminus to the amino terminus of an intein selected from the group consisting of a native intein, an intein derivative, and a mutant intein, wherein the intein is optionally fused to a binding protein domain at its carboxy terminus;
   (b) inducing cleavage of the intein from the target protein by contacting the precursor protein with 2-mercaptoethanesulfonic acid thereby forming a carboxy-terminal thioester on the target protein;
   (c) obtaining the chemically synthesized peptide or protein having an amino terminal cysteine; and,
   (d) ligating the target protein of step (b) to the chemically synthesized peptide or protein of step (c);
thereby forming a modified target protein.

10. The method according to claim 9, wherein the protein after modification is a cytotoxic protein.

11. A method of labeling a target protein comprising:
   (a) expressing a recombinant precursor protein in a host cell, the precursor protein comprising the target protein fused at its carboxy terminus to the amino terminus of an intein, the intein being selected from the group consisting of a native intein, an intein derivative, and a mutant intein, wherein the intein is optionally fused at its carboxy terminus to a binding protein domain;
   (b) inducing cleavage of the intein from the target protein by contacting the precursor protein with 2-mercaptoethanesulfonic acid thereby forming a carboxy-terminal thioester on the target protein;
   (c) obtaining a chemically synthesized peptide or protein having a marker and an amino-terminal cysteine; and,
   (d) ligating the target protein of step (b) to the chemically synthesized peptide or protein of step (c);
thereby forming the labeled target protein.

12. The method according to claim 11, wherein the marker is selected from the group consisting of a fluorescent marker, a spin label, an affinity tag, and a radiolabel.

13. The method according to claim 11, wherein the chemically synthesized peptide or protein is an antigenic determinant.

14. A method of restoring a biological activity to a polypeptide inactive due to the absence of a carboxyl proximal amino acid sequence region by ligating a chemically synthesized protein or peptide comprising a carboxyl proximal amino acid sequence region of the polypeptide to the polypeptide lacking said region, comprising:

(a) expressing a recombinant fusion protein in a host cell, the fusion protein comprising the inactive form of the polypeptide fused at its carboxy terminus to the amino terminus of an intein, the intein being selected from the group consisting of a native intein, an intein derivative, and a mutant intein, wherein the fusion protein is expressed from a plasmid;

(b) inducing cleavage of the intein from the inactive form of the polypeptide by contacting the fusion protein of step (a) with 2-mercaptoethanesulfonic acid thereby forming a carboxy-terminal thioester on the inactive form of the polypeptide;

(c) obtaining a chemically synthesized peptide or protein having an amino-terminal cysteine; and, (d) ligating the inactive form of the polypeptide having a carboxy-terminal thioester produced in step (b) to the chemically synthesized peptide or protein of step (c); thereby restoring a biological activity of the polypeptide.

15. The method according to claim 14, wherein the polypeptide to which ligation with a carboxyl proximal amino acid sequence region restores a biological activity is a cytotoxic protein.

16. The method of claim 15, wherein the cytotoxic protein is a restriction endonuclease.

* * * * *

UNITED STATES PATENT AND TRADEMARK OFFICE
CERTIFICATE OF CORRECTION

PATENT NO. : 7,001,745 B1
APPLICATION NO. : 09/786,009
DATED : February 21, 2006
INVENTOR(S) : Ming-qun Xu et al.

It is certified that error appears in the above-identified patent and that said Letters Patent is hereby corrected as shown below:

On title page, item 57 Abstract replace

(57) ABSTRACT

The present invention provides methods that utilize compositions containing colostrinin, an constituent peptide thereof, an active analog thereof, and combinations thereof, as an oxidative stress regulator.

with

(57) Abstract: An in vitro method for producing a semisynthetic fusion protein is provided, whereby a target protein fuse to an intein - a protein splicing element - is selectively cleaved in a first step as depicted in Figure 1 with a thiol reagent, forming a carboxyl-terminal thioester of the target protein and releasing the target protein from the intein. In a subsequent step as shown in Figure 1, a desired, synthetic, protein or peptide having an amino-terminal cysteine is ligated to the target protein. Standard thiol-reagents such as DTT, or thiol-reagents optimized for ligation such as the odorless MESNA, may be used in the first step. The method permits the direct ligation of a desired peptide to a thioester bond that had linked a target protein to an intein. An in vivo variation of the method will permit production of a cytotoxic protein: a truncated, inactive, form of the protein fused to an intein is introduced in vivo, this fusion product is then selectively cleaved, and a synthetic protein or peptide is subsequently ligated at a carboxyl-terminal thioester of the target protein in order to restore the native activity of the cytotoxic protein.

Signed and Sealed this

Twenty-sixth Day of December, 2006

JON W. DUDAS
*Director of the United States Patent and Trademark Office*

SEQUENCE LISTING

<160> NUMBER OF SEQ ID NOS: 9

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: the
      modified C-terminal splice junction of the  intein from the
      gyrA gene of Mycobacterium xenopi

<400> SEQUENCE: 1
ggttcgtcag ccacgctact ggcctcaccg gttgatagct gca                             43

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: the
complementary strand of the C-terminal splice
junction of the modified intein from the gyrA
gene of Mycobacterium xenopi

<400> SEQUENCE: 2
gctatcaacc ggtgaggcca gtagcgtggc tgacgaacc                    39

<210> SEQ ID NO 3
<211> LENGTH: 68
<212> TYPE: DNA
<213> ORGANISM: Artificial Sequence
<220> FEATURE:
<223> OTHER INFORMATION: Description of Artificial Sequence: the
polylinker sequence inserted upstream of the modified intein
from the gyrA gene of Mycobacterium xenopi

<400> SEQUENCE: 3
tcgaatctag acatatggcc atgggtggcg gccgcctcga gggctcttcc tgcatcacgg    60
gagatgca                                                           68

<210> SEQ ID NO 4
<211> LENGTH: 69
<212> TYPE: DNA
<213> ORGANISM: Artificial Sequence
<220> FEATURE:
<223> OTHER INFORMATION: At position 41, "H" = A or C or T.
<223> OTHER INFORMATION: Description of Artificial Sequence: the
complementary strand of the polylinker inserted
upstream of the modified intein from the gyrA
gene of Mycobacterium xenopi

<400> SEQUENCE: 4
ctagtgcatc tcccgtgatg caggaagagc cctcgaggcg hgccgccacc catggccata    60
tgtctagat                                                          69

<210> SEQ ID NO 5
<211> LENGTH: 6509
<212> TYPE: DNA
<213> ORGANISM: Artificial Sequence
<220> FEATURE:
<223> OTHER INFORMATION: Description of Artificial Sequence: pTXB1
plasmid sequence containing the modified intein from the
gyrA gene of Mycobacterium xenopi

<400> SEQUENCE: 5
aactacgtca ggtggcactt ttcggggaaa tgtgcgcgga acccctattt gtttattttt    60
ctaaatacat tcaaatatgt atccgctcat gagacaataa ccctgataaa tgcttcaata   120
atattgaaaa aggaagagta tgagtattca acatttccgt gtcgccctta ttcccttttt   180
tgcggcattt tgccttcctg ttttgctca cccagaaacg ctggtgaaag taaagatgc    240 tgaagatcag ttgggtgcac gagtgggtta catcgaactg gatctcaaca gcggtaagat   300
ccttgagagt tttcgccccg aagaacgttc tccaatgatg agcactttta aagttctgct   360
atgtggcgcg gtattatccc gtgttgacgc cgggcaagag caactcggtc gccgcataca   420
ctattctcag aatgacttgg ttgagtactc accagtcaca gaaaagcatc ttacggatgg   480
catgacagta agagaattat gcagtgctgc cataaccatg agtgataaca ctgcggccaa   540
cttacttctg acaacgatcg gaggaccgaa ggagctaacc gcttttttgc acaacatggg   600

-continued

```
ggatcatgta actcgccttg atcgttggga accggagctg aatgaagcca taccaaacga    660
cgagcgtgac accacgatgc ctgtagcaat ggcaacaacg ttgcgcaaac tattaactgg    720
cgaactactt actctagctt cccggcaaca attaatagac tggatggagg cggataaagt    780
tgcaggacca cttctgcgct cggcccttcc ggctggctgg tttattgctg ataaatctgg    840
agccggtgag cgtgggtctc gcggtatcat tgcagcactg gggccagatg gtaagccctc    900
ccgtatcgta gttatctaca cgacggggag tcaggcaact atggatgaac gaaatagaca    960
gatcgctgag ataggtgcct cactgattaa gcattggtaa ctgtcagacc aagtttactc   1020
atatatactt tagattgatt taccccggtt gataatcaga aaagcccaa aaacaggaag    1080
attgtataag caaatattta aattgtaaac gttaatattt tgttaaaatt cgcgttaaat   1140
ttttgttaaa tcagctcatt ttttaaccaa taggccgaaa tcggcaaaat cccttataaa   1200
tcaaaagaat agcccgagat agggttgagt gttgttccag tttggaacaa gagtccacta   1260
ttaaagaacg tggactccaa cgtcaaaggg cgaaaaaccg tctatcaggg cgatggccca   1320
ctacgtgaac catcacccaa atcaagtttt tggggtcga ggtgccgtaa agcactaaat    1380
cggaacccta agggagcccc cgatttaga gcttgacggg gaaagccggc gaacgtggcg    1440
agaaaggaag ggaagaaagc gaaaggagcg ggcgctaggg cgctggcaag tgtagcggtc   1500
acgctgcgcg taaccaccac acccgccgcg cttaatgcgc cgctacaggg cgcgtaaaag   1560
gatctaggtg aagatccttt ttgataatct catgaccaaa atcccttaac gtgagttttc   1620
gttccactga gcgtcagacc ccgtagaaaa gatcaaagga tcttcttgag atccttttt    1680
tctgcgcgta atctgctgct tgcaaacaaa aaaaccaccg ctaccagcgg tggtttgttt   1740
gccggatcaa gagctaccaa ctctttttcc gaaggtaact ggcttcagca gagcgcagat   1800
accaaatact gtccttctag tgtagccgta gttaggccac cacttcaaga actctgtagc   1860
accgcctaca tacctcgctc tgctaatcct gttaccagtg ctgctgcca gtggcgataa    1920
gtcgtgtctt accgggttgg actcaagacg atagttaccg gataaggcgc agcggtcggg   1980
ctgaacgggg ggttcgtgca cacagcccag cttggagcga acgacctaca ccgaactgag   2040
atacctacag cgtgagctat gagaaagcgc cacgcttccc gaagggagaa aggcggacag   2100
gtatccggta agcggcaggg tcggaacagg agagcgcacg agggagcttc caggggggaa   2160
cgcctggtat ctttatagtc ctgtcgggtt tcgccacctc tgacttgagc gtcgattttt   2220
gtgatgctcg tcaggggggc ggagcctatg gaaaaacgcc agcaacgcgg ccttttttacg  2280
gttcctggcc ttttgctggc cttttgctca catgttcttt cctgcgttat cccctgattc   2340
tgtggataac cgtattaccg cctttgagtg agctgatacc gctcgccgca gccgaacgac   2400
cgagcgcagc gagtcagtga gcgaggaagc tatggtgcac tctcagtaca atctgctctg   2460
atgccgcata gttaagccag tatacactcc gctatcgcta cgtgactggg tcatggctgc   2520
gccccgacac ccgccaacac ccgctgacgc gccctgacgg gcttgtctgc tcccggcatc   2580
cgcttacaga caagctgtga ccgtctccgg gagctgcatg tgtcagaggt tttcaccgtc   2640
atcaccgaaa cgcgcgaggc agctgcggta aagctcatca gcgtggtcgt gcagcgattc   2700
acagatgtct gcctgttcat ccgcgtccag ctcgttgagt ttctccagaa gcgttaatgt   2760
ctggcttctg ataaagcggg ccatgttaag gcggttttt tcctgtttgg tcacttgatg    2820
cctccgtgta aggggaatt tctgttcatg ggggtaatga taccgatgaa acgagagagg    2880
atgctcacga tacgggttac tgatgatgaa catgcccggt tactggaacg ttgtgagggt   2940
```

-continued

```
aaacaactgg cggtatggat gcggcgggac cagagaaaaa tcactcaggg tcaatgccag    3000
ccgaacgcca gcaagacgta gcccagcgcg tcggccgcca tgccggcgat aatggcctgc    3060
ttctcgccga aacgtttggt ggcgggacca gtgacgaagg cttgagcgag ggcgtgcaag    3120
attccgaata ccgcaagcga caggccgatc atcgtcgcgc tccagcgaaa gcggtcctcg    3180
ccgaaaatga cccagagcgc tgccggcacc tgtcctacga gttgcatgat aaagaagaca    3240
gtcataagtg cggcgacgat agtcatgccc cgcgcccacc ggaaggagct gactgggttg    3300
aaggctctca agggcatcgg tcgagatccc ggtgcctaat gagtgagcta acttacatta    3360
attgcgttgc gctcactgcc cgcttttcag tcgggaaacc tgtcgtgcca gctgcattaa    3420
tgaatcggcc aacgcgcggg gagaggcggt ttgcgtattg ggcgccaggg tggttttttct   3480 tttcaccagt gagacgggca acagctgatt gcccttcacc gcctggccct gagagagttg    3540
cagcaagcgg tccacgctgg tttgccccag caggcgaaaa tcctgtttga tggtggttaa    3600
cggcgggata taacatgagc tgtcttcggt atcgtcgtat cccactaccg agatatccgc    3660
accaacgcgc agcccggact cggtaatggc gcgcattgcg cccagcgcca tctgatcgtt    3720
ggcaaccagc atcgcagtgg gaacgatgcc ctcattcagc atttgcatgg tttgttgaaa    3780
accggacatg gcactccagt cgccttcccg ttccgctatc ggctgaattt gattgcgagt    3840
gagatattta tgccagccag ccagacgcag acgcgccgag acagaactta atgggcccgc    3900
taacagcgcg atttgctggt gacccaatgc gaccagatgc tccacgccca gtcgcgtacc    3960
gtcttcatgg gagaaaataa tactgttgat gggtgtctgg tcagagacat caagaaataa    4020
cgccggaaca ttagtgcagg cagcttccac agcaatggca tcctggtcat ccagcggata    4080
gttaatgatc agcccactga cgcgttgcgc gagaagattg tgcaccgccg ctttacaggc    4140
ttcgacgccg cttcgttcta ccatcgacac caccacgctg gcacccagtt gatcggcgcg    4200
agatttaatc gccgcgacaa tttgcgacgg cgcgtgcagg gccagactgg aggtggcaac    4260
gccaatcagc aacgactgtt tgcccgccag ttgttgtgcc acgcggttgg gaatgtaatt    4320
cagctccgcc atcgccgctt ccactttttc ccgcgttttc gcagaaacgt ggctggcctg    4380
gttcaccacg cgggaaacgg tctgataaga gacaccggca tactctgcga catcgtataa    4440
cgttactggt ttcacattca ccaccctgaa ttgactctct tccgggcgct atcatgccat    4500
accgcgaaag gttttgcgcc attcgatggt gtcccggatc tcgacgctct cccttatgcg    4560
actcctgcat taggaagcag cccagtagta ggttgaggcc gttgagcacc gccgccgcaa    4620
ggaatggtgc atgccgccct tcgtcttca agaattaatt cccaattcca ggcatcaaat    4680
aaaacgaaag gctcagtcga aagactgggc ctttcgtttt atctgttgtt tgtcggtgaa    4740
cgctctcctg agtaggacaa atccgccggg agcggatttg aacgttgcga agcaacggcc    4800
cggagggtgg cgggcaggac gcccgccata aactgccagg aattaattcc aggcatcaaa    4860
taaaacgaaa ggctcagtcg aaagactggg cctttcgttt tatctgttgt ttgtcggtga    4920
acgctctcct gagtaggaca aatccgccgg gagcggattt gaacgttgcg aagcaacggc    4980
ccggagggtg gcgggcagga cgcccgccat aaactgccag gaattaattc caggcatcaa    5040
ataaaacgaa aggctcagtc gaaagactgg gcctttcgtt ttatctgttt ttgtcggtg    5100 aacgctctcc tgagtaggac aaatccgccg ggagcggatt tgaacgttgc gaagcaacgg    5160
cccggagggt ggcgggcagg acgcccgcca taaactgcca ggaattaatt ccaggcatca    5220
aataaaacga aaggctcagt cgaaagactg ggcctttcgt tttatctgtt gtttgtcggt    5280
gaacgctctc ctgagtagga caaatccgcc gggagcggat ttgaacgttg cgaagcaacg    5340
```

```
gcccggaggg tggcgggcag gacgcccgcc ataaactgcc aggaattggg gatcggaatt      5400
aattcccggt ttaaaccggg gatctcgatc ccgcgaaatt aatacgactc actatagggg      5460
aattgtgagc ggataacaat tcccctctag aaataatttt gtttaacttt aagaaggaga      5520
tatacatatg gctagctcgc gagtcgacgg cggccgcgaa ttcctcgagg gctcttcctg      5580
catcacggga gatgcactag ttgccctacc gagggcgag tcggtacgca tcgccgacat       5640
cgtgccgggt gcgcggccca acagtgacaa cgccatcgac ctgaaagtcc ttgaccggca      5700
tggcaatccc gtgctcgccg accggctgtt ccactccggc gagcatccgg tgtacacggt      5760
gcgtacggtc gaaggtctgc gtgtgacggg caccgcgaac cacccgttgt tgtgtttggt      5820
cgacgtcgcc ggggtgccga ccctgctgtg gaagctgatc gacgaaatca gccgggcga      5880 ttacgcggtg attcaacgca gcgcattcag cgtcgactgt gcaggttttg cccgcgggaa      5940
acccgaattt gcgcccacaa cctacacagt cggcgtccct ggactggtgc gtttcttgga      6000
agcacaccac cgagacccgg acgcccaagc tatcgccgac gagctgaccg acgggcggtt      6060
ctactacgcg aaagtcgcca gtgtcaccga cgccggcgtg cagccggtgt atagccttcg      6120
tgtcgacacg gcagaccacg cgtttatcac gaacgggttc gtcagccacg ctactggcct      6180
caccggtctg aactcaggcc tcacgacaaa tcctggtgta tccgcttggc aggtcaacac      6240
agcttatact gcgggacaat tggtcacata taacggcaag acgtataaat gtttgcagcc      6300
ccacacctcc ttggcaggat gggaaccatc caacgttcct gccttgtggc agcttcaatg      6360
actgcaggaa ggggatccgg ctgctaacaa agcccgaaag gaagctgagt tggctgctgc      6420
caccgctgag caataactag cataaccccct tggggcctct aaacgggtct tgagggggttt     6480 tttgctgaaa ggaggaacta tatccggat                                         6509
```

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 6

Cys Ala Tyr Lys Thr Thr Gln Ala Asn Lys His Ile Ile Val Ala Cys
 1               5                  10                  15

Glu Gly Asn Pro Tyr Val Pro Val His Phe Asp Ala Ser Val
            20                  25                  30

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: the amino
      acid sequence deduced from the polylinker region of
      pTXB1

<400> SEQUENCE: 7

Met Ala Met Gly Gly Gly Arg Leu Glu Gly Ser Ser Cys
 1               5                  10

<210> SEQ ID NO 8
<211> LENGTH: 42
<212> TYPE: DNA
<213> ORGANISM: Artificial Sequence
<220> FEATURE:

-continued

```
<223> OTHER INFORMATION: Description of Artificial Sequence: polylinker
      region upstream of the modified intein from the
      gyrA gene of Mycobacterium xenopi in pTXB1

<400> SEQUENCE: 8
catatggcca tgggtggcgg ccgcctcgag ggctcttcct gc                           42

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 9

Cys Asp Pro Glu Lys Asp Ser
 1               5
```